Figure 1:
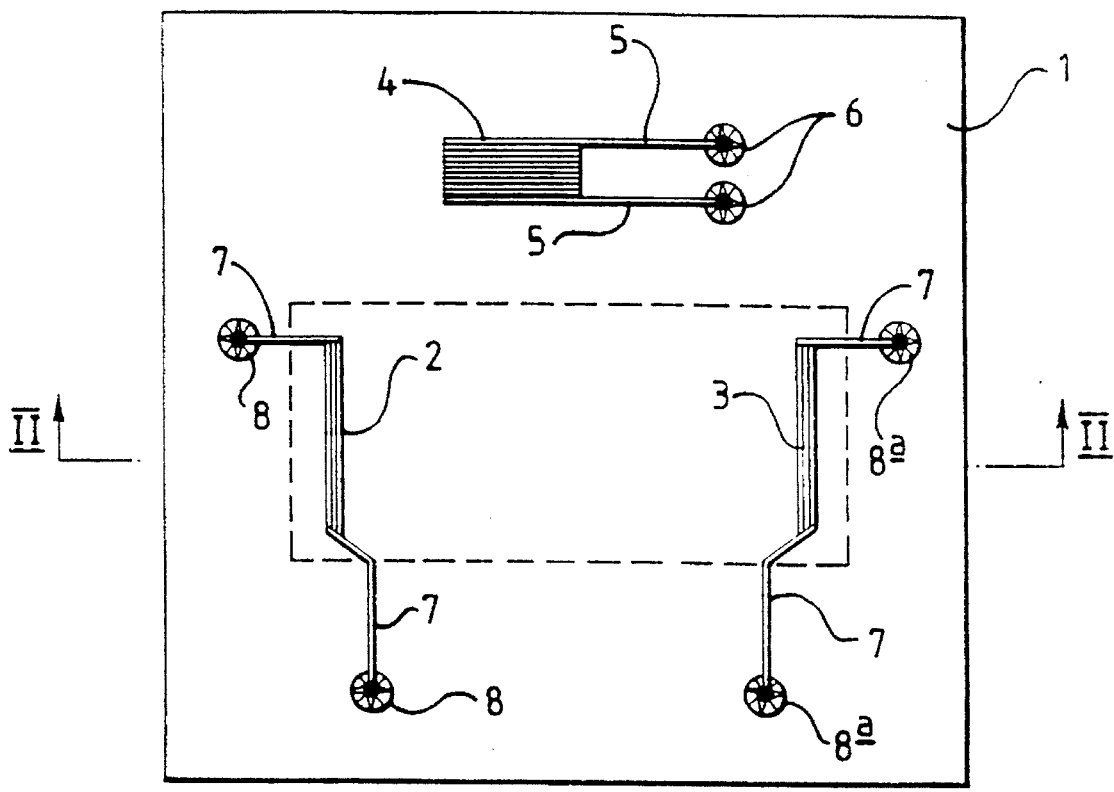

United States Patent [19]
Gizeli et al.

[11] Patent Number: 5,478,756
[45] Date of Patent: Dec. 26, 1995

[54] CHEMICAL SENSOR FOR DETECTING BINDING REACTIONS

[75] Inventors: Electra Gizeli, London; Adrian C. Stevenson, Cambridge, both of England

[73] Assignees: Fisons plc; GEC Marfoni Limited, Ipswich, England

[21] Appl. No.: 385,737

[22] Filed: Feb. 8, 1995

Related U.S. Application Data

[63] Continuation of Ser. No. 975,583, filed as PCT/GB91/01203 Jul. 18, 1991, abandoned.

[30] Foreign Application Priority Data

Jul. 24, 1990 [GB] United Kingdom .................. 9016177

[51] Int. Cl.⁶ .................................................. G01N 33/552
[52] U.S. Cl. .......................... 436/527; 73/587; 73/590; 73/645; 73/649; 310/311; 310/312; 310/313 R; 310/313 A; 310/313 B; 310/313 D; 310/316; 310/317; 310/318; 310/319; 310/327; 310/334; 310/340; 310/345; 310/363; 310/367; 422/82.01; 426/518; 426/524; 426/149; 426/806
[58] Field of Search .............................. 73/587, 590, 618, 73/620, 627, 645, 649; 310/311, 312, 313 R, 313 A, 313 B, 313 D, 315–319, 327, 334, 340, 345, 363–367; 422/82.01; 436/518, 524, 527, 149, 151, 806

[56] References Cited

U.S. PATENT DOCUMENTS

| | | | |
|---|---|---|---|
| 4,210,722 | 7/1980 | Silver | 310/311 |
| 4,236,893 | 12/1980 | Rice | 310/312 |
| 4,242,096 | 12/1980 | Oliveira et al. | 310/312 |
| 4,312,228 | 1/1982 | Wohltjen | 73/597 |
| 4,314,821 | 2/1982 | Rice | 310/312 |
| 4,484,098 | 11/1984 | Cullen et al. | 310/313 A |
| 4,523,122 | 6/1985 | Tone et al. | 310/327 |
| 4,544,857 | 10/1985 | Shimizu et al. | 310/313 A |
| 4,680,499 | 7/1987 | Umemura et al. | 310/327 |
| 4,735,906 | 4/1988 | Bastiaans | 436/527 |
| 4,847,193 | 7/1989 | Richards et al. | 436/531 |
| 4,999,284 | 3/1991 | Ward et al. | 436/531 |
| 5,130,257 | 7/1992 | Baer et al. | 436/151 |

FOREIGN PATENT DOCUMENTS

| | | |
|---|---|---|
| 0246346 | 11/1987 | European Pat. Off. . |
| 0361729 | 4/1990 | European Pat. Off. . |

OTHER PUBLICATIONS

*Analytical Chemistry,* vol. 58, No. 14, 1 Dec. 1986, D. Balantine et al. "Correlation of surface acoustic wave device coating responses with solubility properties and chemical structure using pattern," pp. 3058–3066, see table II.

*Primary Examiner*—David Saunders
*Assistant Examiner*—Christopher L. Chin
*Attorney, Agent, or Firm*—Marshall, O'Toole, Gerstein, Murray & Borun

[57] ABSTRACT

A chemical sensor includes a piezoelectric support (1) capable of supporting a shear horizontal wave provided on its surface with an electrode (2,3). The sensor is characterized in that the surface of the piezoelectric support (1) including the region bearing the electrode (2,3) is covered by a layer of dielectric material (9) of thickness 0.5 to 20 microns. The piezoelectric support (1) is preferably a single crystal. The dielectric layer (1) may be of, for example, silicon dioxide or a suitable polymer, and preferably has a thickness of between 0.5 and 5 μm.

13 Claims, 2 Drawing Sheets

CHEMICAL SENSOR FOR DETECTING BINDING REACTIONS

This is a continuation of U.S. application Ser. No. 07/975,583, filed as PCT/GB91/01203 Jul. 18, 1991, now abandoned.

This invention relates to chemical sensors, in particular to biosensors for detecting, for example, antibody-antigen binding reactions.

Antibodies are molecules which protect an organism from disease and/or infection. When an organism is exposed to an antigen, the organism creates antibodies which provide binding sites to which the antigen may be bound and immobilised.

Many known antibodies exist and can be used to detect specific antigens. Detection of such antigens is effected by providing the appropriate antibody and determining whether binding takes place. For example, an antibody may be provided on a surface of a support, the support may be immersed in a liquid thought to contain an antigen, and a physical characteristic of the surface and/or the support monitored to determine if binding (indicative of the presence of the antigen) has taken place. One form of support which has been used is a piezo-electric crystal in which surface acoustic waves (SAW) are generated. Binding of antigen to antibody on the surface of the support is detected as a decrease in wave velocity.

A problem which occurs with known SAW sensors is that considerable penetration occurs of the acoustic wave into the environment to be sensed. If the environment is gaseous this problem is not unduly onerous. However, if (as is usually the case for analysis of biologically originating samples) the environment is liquid then the penetration of the wave into the environment causes considerable damping. This in turn reduces the sensitivity of the device.

Devices have also been described which utilize shear horizontal waves. These offer a number of advantages over SAW devices:
1. Bulk waves suffer lower propagation losses than SAW (under liquids),
2. Bulk waves have higher velocities and can therefore be used at higher frequencies than SAW,
3. Bulk waves have superior temperature coefficients to SAW in both quartz and $LiTaO_3$.

However, these bulk wave devices suffer from the disadvantage of a limited mass sensitivity due to poor surface energy confinement.

We have now devised an improved form of chemical sensor of particular utility in the detection and/or determination of an analyte species in a sample which is liquid, as is generally the case for samples of biological origin, and which overcomes or substantially mitigates the disadvantages associated with known SAW and bulk wave devices.

According to the invention, there is provided a chemical sensor comprising;
 a piezoelectric support capable of supporting a shear horizontal wave provided on its surface with an electrode,
 characterized in that the surface of the piezoelectric support including the region bearing the electrode is covered by a layer of dielectric material of thickness 0.5 to 20 microns.

The sensor according to the invention is advantageous in that the layer of dielectric material increases the coupling coefficient and reduces the insertion loss of the wave. Also, and very importantly, the device may be totally immersed in a liquid with little attenuation occurring in the intensity of the guided surface wave.

Other advantages of the sensor according to the invention include its relatively simple construction and the face that the whole surface of the device may be used for sensing, which increases the sensitivity. The dielectric layer may also reduce the temperature coefficient of delay. Further, by appropriate choice of dielectric material, eg derivatised silica, the need for an adhesion layer for the immobilisation of reagents on the surface can be eliminated.

The piezoelectric support may be formed of any suitable piezoelectric material. Generally, suitable materials will have the following properties:
1. Large surface shear horizontal displacement,
2. Large electromechanical coupling constant,
3. Zero or small piezoelectric coupling to SAW and other bulk waves,
4. Zero or small beam steering both on the surface and into the bulk,
5. Zero or small temperature coefficient of delay.

Examples of suitable materials include lithium tantalate and quartz. The material is preferably a single crystal, particularly a single crystal cut in such a manner that waves polarized horizontally (ie in planes parallel to the surface of the support) are favoured. The thickness of the piezoelectric support is generally not critical but is typically of the order of 0.5 mm for ease of handling. A reflecting lower surface could result in a plate-mode configuration which is not preferred. The support may alternatively comprise a slab of non-piezoelectric material with a thin layer of piezoelectric material coated on its surface.

The device according to the invention is conveniently a two-port waveguide sensor having spaced apart input and output electrodes. Alternatively, the device may be a one-port resonator having a single electrode with a reflective metallic grating on either side. The gratings reflect the acoustic waves, a resonant cavity being formed between the gratings. Also, the gratings effect mass loading of the surface. For this latter purpose, a grating may be included in the two-port device, between the input and output electrodes.

The electrode(s) may take any conventional form but are preferably photolithographically deposited on the surface as elongate regions of metallisation transverse to the direction of propagation of a wave along the surface of the support. The elongate metallised regions preferably have a width and spacing of the same order of magnitude, the width being typically between 1 and 40 µm, preferably between 10 and 20 µm.

The regions of metallisation forming the electrodes may be formed by the deposition of chromium on the surface of the support and the vapour deposition of gold onto the chromium, and thereafter by etching to the desired pattern.

The thickness of the electrode(s) is typically between 0.1 and 5 µm, preferably of the order of 0.2 µm.

The surface of the piezoelectric support opposite no the surface carrying the electrode(s) is preferably coated or intimately contacted with a material having a good impedance match with the piezoelectric material and high acoustic absorption. This is to ensure that acoustic energy propagated through the piezoelectric material is not reflected back towards the active surface of the device. Suitable materials include plastics, wax and silicone rubber.

The dielectric layer may be formed of any suitable dielectric material. Suitable materials will have the property that the acoustic velocity in the dielectric is lower than that in the piezoelectric substrate. Examples of suitable materials include silicon dioxide and certain polymers, e.g. polymethylmethacrylate, polytetrafluoroethylene, polystyrene and polyethylene. Where polymers are used, they are preferably cross-linked to reduce infiltration of the layer by water molecules from the sample under test.

The optimum thickness of the dielectric layer will depend on numerous factors including the particular material used but in general satisfactory results are obtained with a layer of thickness 0.5 to 5 µm, typically 1 to 3 µm.

The dielectric layer is mechanically stiff to couple to the motion of the support and sufficiently dense to minimise waves lost to the support.

The dielectric layer is preferably derivatised or activated to facilitate immobilisation thereon of suitable binding reagents for the analyte(s) under test. Such reagents include, for biological samples, antibodies or antigens, and for other chemical applications such species as crown ethers (for the determination of particular ionic species), In the operation of a two port device, an electrical signal, typically with a frequency of the order of 100 MHz, is applied to the input electrode which acts as a transducer, converting the electrical signal into an acousto-electric signal. Electrical matching circuitry is preferably provided to ensure efficient conversion of the radiofrequency signal into the acousto-electric signal which travels as a plane wave from the input electrode to the output electrode. Electrical matching is preferably carried out by means of a tuned core transformer or, more preferably, a low-loss balun.

The output electrode converts the acoustic signal back into a radiofrequency electric signal. Mass binding or viscous coupling to the vibrating surface as a result of a chemical or biochemical reaction slows down the surface wave and is detected as a change in signal phase (mass binding) or signal attenuation (viscous coupling). The phase change due to mass binding can be detected by frequency ratioing, a network analyser or similar phase detection system. The phase detector preferably includes a phase-locked loop system to maintain the phase of the signal constant, thereby improving the signal to noise ratio. The surface dielectric layer ensures that the transmitted wave is slowed so that energy that would otherwise radiate down into the crystal bulk is retained at the surface of the piezo-electric crystal. This in turn increases the sensitivity of the device.

Figure 2:
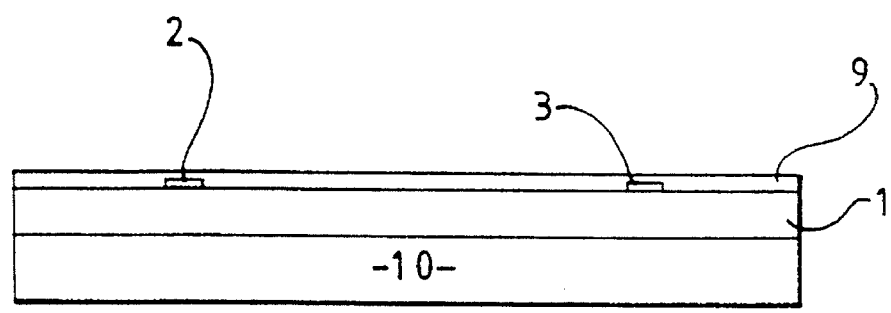
Figure 3:
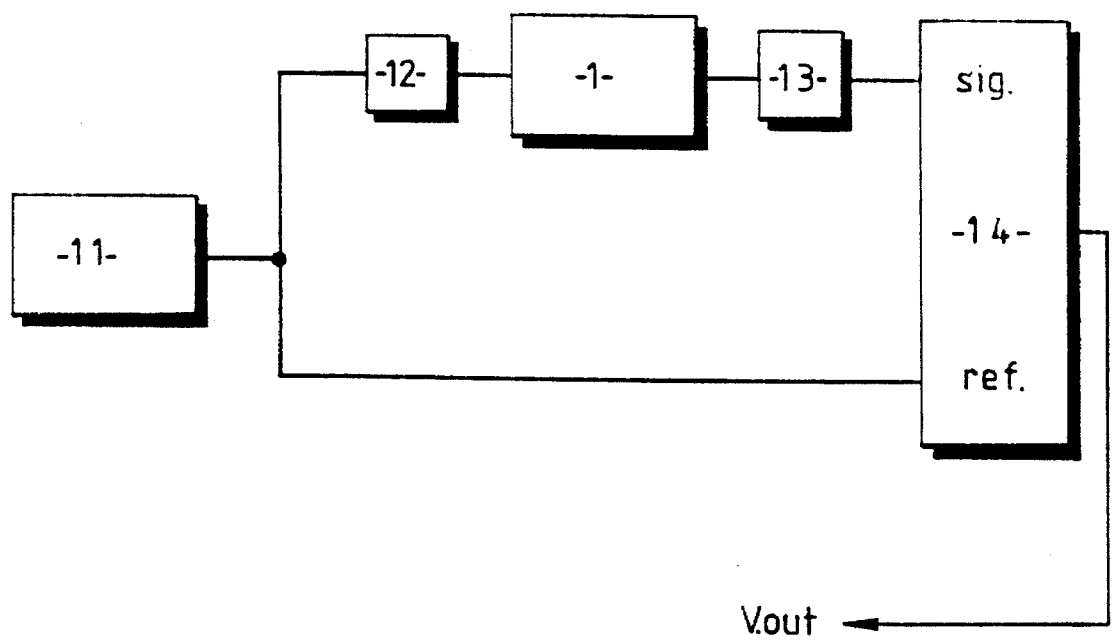

A preferred embodiment of a chemical sensor according to the invention will now be described, by way of illustration only, with reference to the accompanying drawings in which FIG. 1 is a plan view of the uncoated surface of a chemical sensor according to the invention, FIG. 2 is a cross-sectional view along the line II—II in FIG. 1, and FIG. 3 is a schematic representation of a sensing device incorporating the sensor of FIG. 1.

Referring first to FIG. 1, a chip (1) of a single quartz crystal of approximate thickness 0.5 mm forms a support for the sensor. The crystal is cut on the ST axis and the surface is polished and the underside preferably roughened. First and second electrodes (2,3) are deposited on the surface parallel to the X-axis of the crystal. The electrodes (2,3) are formed by photolithographic techniques, eg deposition and subsequent etching, and comprise parallel strips having a thickness of approximately 200 nm, a width of approximately 11 µm, and a spacing of approximately 20 µm. The electrodes may be formed by the initial deposition of a layer of chromium. A layer of gold is then vapour deposited onto the surface of the chromium. The electrode pattern is then defined photolithographically using a resist and etched.

The chip also includes a temperature sensing device (4) having leads (5) and contact pads (6). The dimensions of the chip are approximately 10 mm×10 mm but is will be appreciated that a number of such devices are formed simultaneously on a wafer of quartz, the individual chips being cut from the wafer at a later stage of manufacture.

The electrodes (2,3) are brought out by connectors (7) to contact pads (8, 8a).

As can be seen from FIG. 2, the chip (1) is provided on its surface bearing the electrodes (2,3) with a layer of silicon dioxide (9), and on the opposite surface with a coating of acoustically absorbing plastics tape (10). The layer of silicon dioxide (9) is approximately 3 µm in thickness and covers the whole top surface of the chip (1) including the first and second electrodes (2,3).

Immobilised on the surface (within the area defined by the dashed line in FIG. 1) of the layer of silicon dioxide (9) are appropriate binding reagents for the analyte under test. Such immobilisation can be carried out by techniques which are known to those skilled in the art.

In use, an AC signal of radiofrequency, say 100 MHz, is applied from a synthesised oscillator (11) via electrical matching circuitry (12) to the contact pads (8) of the first electrode (2). This causes the production of motion in the crystal and the transmission of a guided acoustic wave along the surface of the crystal transverse to the X-axis and the electrodes (2,3). The operating frequency is determined by the velocity of the surface wave divided by twice the finger separation of the electrodes (2,3).

The guided acoustic wave is converted back into an electric signal by the second electrode (3) and is passed via further matching circuitry (13) to a phase detection system (14) which produces an output voltage ($V_{out}$) proportional to the difference in phase of reference and signal.

In use, the device is immersed in a liquid to be tested, or a drop of liquid is applied to the surface of the layer of silicon dioxide (9). If the liquid contains the species which binds with the reagent immobilised on the surface of the layer (9), a change in mass occurs at that surface. This slows the acoustic wave and alters the phase of the output signal. The change in phase provides a quantitative indication of the presence of the analyte in the sample.

We claim:

1. A chemical sensor comprising:

a piezoelectric support having a surface;

at least two electrodes spaced apart on said surface of said piezoelectric support;

a layer of dielectric material of thickness 0.5 to 20 microns applied to said surface of said piezoelectric support so as to cover at least said electrodes and a region of said surface intermediate said electrodes; and a layer of specific active reagent immobilized on said layer of dielectric material and at least intermediate said electrodes, wherein, in use of said sensor, a shear horizontal wave can be supported at said surface of said piezoelectric support.

2. A sensor as claimed in claim 1, wherein said piezoelectric support is a single crystal.

3. A sensor as claimed in claim 2, wherein said piezoelectric support comprises lithium tantalate or quartz.

4. A sensor as claimed in claim 1, which is a two-port waveguide sensor, wherein one of said electrodes is an input electrode and another of said electrodes is an output electrode.

5. A sensor as claimed in claim 4, wherein a metallic grating is provided between said input and output electrodes.

6. A sensor as claimed in claim 1, wherein said electrodes are photolithographically deposited on said surface as elongate regions of metallization transverse to the direction of propagation of a wave along said surface of said support.

7. A sensor as claimed in claim 6, wherein said elongate metallized regions have a width and spacing of between 1 and 40 μm.

8. A sensor as claimed in claim 1, wherein the thickness of said electrodes is between 0.1 and 5 μm.

9. A sensor as claimed in claim 1, wherein a surface of said piezoelectric support opposite to said surface carrying said electrodes is coated or intimately contacted with a material having a good impedance match with the material of said piezoelectric support and high acoustic absorption.

10. A sensor as claimed in claim 1, wherein said layer of dielectric material is of silicon dioxide.

11. A sensor as claimed in claim 1, wherein said layer of dielectric material is polymeric.

12. A sensor as claimed in claim 1, wherein the thickness of said layer of dielectric material is between 0.5 and 5 μm.

13. A sensor as claimed in claim 1, wherein said layer of dielectric material is derivatized or activated to facilitate immobilization thereon of said layer of specific active reagent.

* * * * *

UNITED STATES PATENT AND TRADEMARK OFFICE
CERTIFICATE OF CORRECTION

PATENT NO.  : 5,478,756

DATED       : December 26, 1995

INVENTOR(S) : ELECTRA GIZELI ET AL.

It is certified that error appears in the above-identified patent and that said Letters Patent is hereby corrected as shown below:

Column 2, line 5, "face" should be --fact--

Column 2, line 54, "no" should be --to--

Column 3, line 39, "The" should start a new paragraph

Column 4, line 3, "is" should be --it--

Signed and Sealed this

Second Day of April, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,478,756
DATED : December 26, 1995
INVENTOR(S) : Gizeli et al.

It is certified that error appears in the above-identified patent and that said Letters Patent is hereby corrected as shown below:

On the title page:

Item: [73], "Marfoni" should be --Marconi--

Signed and Sealed this

Sixteenth Day of July, 1996

BRUCE LEHMAN

*Attest:*

*Attesting Officer*            *Commissioner of Patents and Trademarks*